United States Patent
Seeber et al.

(10) Patent No.: US 11,862,320 B2
(45) Date of Patent: Jan. 2, 2024

(54) CONTROL DEVICE FOR CONTROLLING AT LEAST ONE COLLIMATOR

(71) Applicant: Deutsches Krebsforschungszentrum, Heidelberg (DE)

(72) Inventors: Steffen Seeber, Heidelberg (DE); Joao Graca, Heidelberg (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 733 days.

(21) Appl. No.: 15/733,725

(22) PCT Filed: Apr. 10, 2019

(86) PCT No.: PCT/EP2019/059030
§ 371 (c)(1),
(2) Date: Oct. 6, 2020

(87) PCT Pub. No.: WO2019/197440
PCT Pub. Date: Oct. 17, 2019

(65) Prior Publication Data
US 2021/0166801 A1    Jun. 3, 2021

(30) Foreign Application Priority Data

Apr. 11, 2018  (EP) .................................... 18166774

(51) Int. Cl.
*G05B 19/05* (2006.01)
*G16H 20/40* (2018.01)
*G05B 19/4155* (2006.01)

(52) U.S. Cl.
CPC ............. *G16H 20/40* (2018.01); *G05B 19/05* (2013.01); *G05B 19/4155* (2013.01); *G05B 2219/1215* (2013.01); *G05B 2219/45169* (2013.01)

(58) Field of Classification Search
CPC .... G01H 20/40; G05B 19/05; G05B 19/4155; G05B 2219/1215; A61N 5/1048
See application file for complete search history.

(56) References Cited

U.S. PATENT DOCUMENTS 4,794,629 A    12/1988  Pastyr et al.
7,242,750 B2    7/2007  Tsujita
(Continued)

FOREIGN PATENT DOCUMENTS

WO    2003043698 A1    5/2003
WO    2006119796 A1    11/2006
(Continued)

OTHER PUBLICATIONS

Hashemian, Abdolreza, Mohammad Taghi Bahreyni Toossi, and Shahrokh Nasseri. "Design and Fabrication of the Control Part of a Prototype Multileaf Collimator System." Journal of medical signals and sensors 4.4 (2014): 300-304. (Year: 2014).*

*Primary Examiner* — Patrick H Mackey
(74) *Attorney, Agent, or Firm* — Woodard, Emhardt, Henry, Reeves & Wagner, LLP

(57) ABSTRACT

A control device (110) for controlling at least one collimator is disclosed, wherein the collimator has a plurality of parts being designed for collimating and shaping rays, wherein the rays are generated for treating a predefined body part of a patient, wherein the control device (110) comprises a programmable logic controller (112), a plurality of controller nodes (114), a plurality of device controllers (118), and a plurality of real-time bus interfaces (116). Herein, the programmable logic controller (112) is designated as a first master device (122) with respect to each of the controller nodes (114), wherein the programmable logic controller
(Continued)

Figure 1:
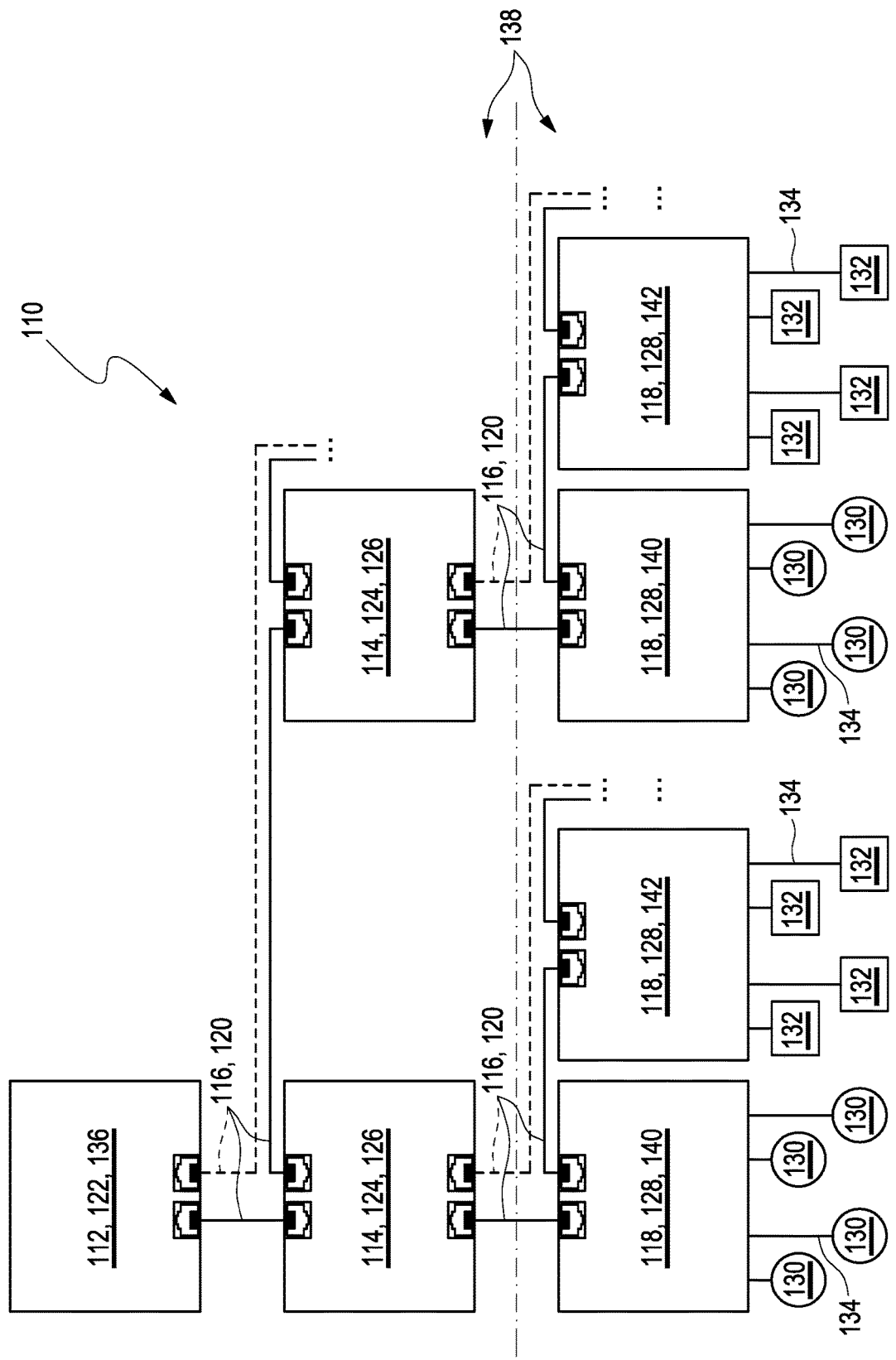

(112) is designed for superordinate control of the plurality of parts of the collimator. Further, each of the controller nodes (114) is designated as a first slave device (124) with respect to the programmable logic controller (112), wherein the controller node (114) is designated as a second master device (126) with respect to at least one corresponding device controller (118), wherein the controller node (114) is designed for controlling at least one corresponding part of the collimator, wherein the controller node (114) is connected to the programmable logic controller (112) by one of the real-time bus interfaces (116). Further, each of the device controllers (118) is designated as a second slave device (128) with respect to a corresponding controller node (114), wherein each of the device controllers (118) is designed for controlling at least one of an actuator (130) and a sensor (132), wherein the actuator (130) is designed for adjusting a corresponding part of the collimator, and wherein the sensor (132) is designed for providing data related to position and/or velocity information with respect to the corresponding part of the collimator, wherein the device controller (118) is connected to the corresponding controller node (114) by one of the real-time bus interfaces (116).

16 Claims, 3 Drawing Sheets

(56) References Cited

U.S. PATENT DOCUMENTS

| | | | |
|---|---|---|---|
| 7,397,054 B2 * | 7/2008 | Natori | A61N 5/1079 |
| | | | 315/504 |
| 8,300,685 B2 * | 10/2012 | Chen | H04L 25/03057 |
| | | | 375/317 |
| 8,992,404 B2 * | 3/2015 | Graf | A61N 5/1048 |
| | | | 600/1 |
| 9,437,340 B2 * | 9/2016 | Echner | A61N 5/1045 |
| 2004/0174958 A1 * | 9/2004 | Moriyama | A61N 5/1079 |
| | | | 600/1 |
| 2005/0141671 A1 | 6/2005 | Pastyr et al. | |
| 2008/0159478 A1 | 7/2008 | Keall et al. | |
| 2008/0191583 A1 | 8/2008 | Bohn | |
| 2009/0041199 A1 | 2/2009 | Bohn | |
| 2009/0074148 A1 | 3/2009 | Echner | |
| 2010/0231962 A1 * | 9/2010 | Sakai | G03G 15/50 |
| | | | 358/1.15 |
| 2010/0278310 A1 | 11/2010 | Dehler et al. | |
| 2014/0288349 A1 * | 9/2014 | Seeber | A61N 5/1045 |
| | | | 600/1 |

FOREIGN PATENT DOCUMENTS

| | | |
|---|---|---|
| WO | 2011130412 A2 | 10/2011 |
| WO | 2013014260 A1 | 1/2013 |

\* cited by examiner

CONTROL DEVICE FOR CONTROLLING AT LEAST ONE COLLIMATOR

TECHNICAL FIELD OF THE INVENTION

The invention relates to a control device for controlling at least one collimator, wherein the collimator has a plurality of parts being designed for collimating and shaping rays, wherein the rays are generated for treating a predefined body part of a patient. The control device according to the present invention may, specifically, be used in a therapeutic device for cancer-treatment. However, other applications are possible.

RELATED ART

For defining a body part which is to be exposed to a radiation treatment, various devices are known for collimating and shaping rays. Thus, so-called "multi-leaf collimators" are widely used for shielding the rays from a selected area and for defining an area of treatment. Examples of multi-leaf collimators for radiation treatment are disclosed in U.S. Pat. No. 4,794,629, WO 03/043 698 A, WO 2006/119796 A1, US 2010/0278310 A1, U.S. Pat. No. 7,242,750 B2, US 2008/0191583 A1, or US 2009/0041199 A1.

US 2008/159478 A1 discloses a method of continuous real-time monitoring and positioning of multi-leaf collimators during on and off radiation exposure conditions of radiation therapy to account for target motion relative to a radiation beam. A prediction algorithm estimates future positions of a target relative to the radiation source. Target geometry and orientation are determined relative to the radiation source. Target, treatment plan, and leaf width data, and temporal interpolations of radiation doses are sent to the controller. Coordinates having an origin at an isocenter of the isocentric plane establish initial aperture end positions of the leaves that is provided to the controller, where motors to position the MLC midpoint aperture ends according to the position and target information. Each aperture end intersects a single point of a convolution of the target and the isocenter of the isocentric plane. Radiation source hold-conditions are provided according to predetermined undesirable operational and/or treatment states.

WO 2011/130412 A2 discloses radiation treatment systems with enhanced control architectures that enable more complex treatment plans to be implemented, and radiation treatment systems with enhanced resistance to the effect of neutrons. An exemplary control architectures comprises: a digital packet network; a supervisor electrically coupled to the digital packet network and having a treatment plan; and a plurality of nodes, each node coupled to digital packet network and controlling one or more treatment-related components of the radiation treatment system; and wherein the supervisor periodically communicates control orders to the nodes over the digital packet network.

WO 2013/014260 A1 discloses a therapeutic device and a method for treating a predefined body part of a patient with rays. The therapeutic device has at least one ray source for generating the rays. The therapeutic device further has at least one collimator for collimating and shaping the rays. The therapeutic device further has at least one ray positioning system for adjusting the position and direction of irradiating the rays onto the patient. The therapeutic device further has at least one patient positioning system for positioning and orienting the patient. The therapeutic device further comprises a control device. The control device controls at least the collimator, the ray positioning system and the patient positioning system. The control device is a real-time system. Herein, the control device is adapted to perform a role of a master device, wherein the collimator, the ray positioning system and the patient positioning system are adapted to perform a role of a slave device.

Despite the advantages as particularly implied by WO 2013/014260 A1, there still is a need for improvements in controlling collimators in order to allow a highly precise and dynamic treatment with high time resolution and/or time constraints of the collimator, in particular, in order to compensate a movement of a tumor and/or an organ at potential risk in real-time during a treatment process.

PROBLEM TO BE SOLVED

It is therefore an objective of the present invention to provide a control device for controlling at least one collimator which at least partially avoids the disadvantages of known control devices. Specifically, it is desired to provide a control device which allows a highly precise and dynamic treatment with high time resolution and/or time constraints of the collimator, in particular, in order to compensate a movement of a tumor and/or an organ at potential risk in real-time during a treatment process.

SUMMARY OF THE INVENTION

This problem is solved by a control device for controlling at least one collimator according to the independent claim. Preferred embodiments of the invention which may be realized in an isolated way or in any arbitrary combination are disclosed in the dependent claims.

As used in the present specification, the term "comprising" or grammatical variations thereof, such as the term "comprise" are to be taken to specify the presence of stated features, integers, steps or components or groups thereof, but do not preclude the presence or addition of one or more other features, integers, steps, components or groups thereof. The same applies to the term "having" or grammatical variations thereof, which is used as a synonym for the term "comprising".

The present invention refers to a control device for controlling at least one collimator, wherein the collimator has a plurality of parts being designed for collimating and shaping rays, wherein the rays are generated for treating a predefined body part of a patient.

According to the present invention, the control device comprises
a programmable logic controller,
a plurality of controller nodes,
a plurality of device controllers, and
a plurality of real-time bus interfaces,
wherein the programmable logic controller is designated as a first master device with respect to each of the controller nodes, wherein the programmable logic controller is designed for superordinate control of the plurality of parts of the collimator,
wherein each of the controller nodes is designated as a first slave device with respect to the programmable logic controller, wherein the controller node is designated as a second master device with respect to at least one corresponding device controller, wherein the controller node is designed for controlling at least one corresponding part of the collimator, wherein the controller node is connected to the programmable logic controller by one of the real-time bus interfaces, wherein each of the device controllers is designated as a second slave device with respect to a corresponding controller node, wherein each of the device controllers is designed for controlling at least one of an actuator and a sensor, wherein the actuator is designed for adjusting a corresponding part of the collimator, and wherein the sensor is designed for providing data related to position information and/or velocity information with respect to the corresponding part of the collimator, wherein the device controller is connected to the corresponding controller node by one of the real-time bus interfaces.

Thus, the control device according to the present invention is designated for controlling at least one collimator. As generally used, the collimator has at a plurality of parts which is designed for collimating and shaping rays. The rays may be a beam, preferably a narrow beam of radiation, e.g. ionizing radiation, in particular a narrow beam of electromagnetic radiation, preferably suitable for cancer therapy. The rays may be selected from x-rays; γ-rays; ion-rays; α-rays; β-rays; neutral particle rays; neutral atom rays; heavy ion rays; atom rays; cold atom rays; electron rays; positron rays; proton rays; visible light rays; photonic rays; charged particle rays; ionizing radiation; continuous wave laser beams; pulsed laser beams; hadron rays; lepton rays; molecular rays. The rays and/or beams consisting of particles, like ion-rays and/or α-rays and/or β-rays and/or atom rays may have different, preferably stable, most preferably predefined and/or adjustable temperatures and/or velocities. Also other kinds of radiation and/or beams may be used, e.g. also combinations of different rays may be possible.

The rays may be generated by a ray source which may be or comprise a device for generating rays, specifically, a linear particle accelerator (LINAC) and/or another type of particle accelerator, e.g. a synchrotron, and/or a laser and/or a device providing radiation, e.g. a device comprising at least one radioactive material. In the linear particle accelerator (LINAC) electrons may be accelerated, specifically by using a klystron and/or a magnetron, e.g. by using a complex magnet arrangement, in a manner that a beam with energy of about 6 to 30 MeV may be produced. The electrons may be used directly as a ray and/or the electrons may be collided with a target to generate, e.g. to produce, photons, e.g. high-energetic x-rays, preferably a beam of x-rays.

The at least one collimator for collimating and shaping the rays may, preferably, be or comprise at least one of: a multi-leaf collimator; an iris diaphragm collimator, such as described in WO 2006/119796; a pendular collimator, such as described in WO 03/043 698. However, alternatively or additionally, other collimators may be used. For the purpose of blocking the rays, the collimator may have at least 60 leaves, at least 80 leaves or at least 100 leaves and more. For further potential embodiments of the multi-leaf collimator, reference may be made to the above-mentioned prior art documents. However, other embodiments of the collimator and/or of the multi-leaf collimator are feasible.

The rays may be formed by high-energy radiation beams. For this purpose, the collimator may be used as a device for collimating, e.g. increasing the coherence of the rays, and/or for shaping the rays, e.g. controlling a geometric shape, e.g. a diameter, and/or a direction of the rays. The leaves of the multi-leaf collimator may also be called "shutter blades" or "lamellae". The multi-leaf collimator may also be called "contour collimator" since due to the positioning of the leaves, contours of treatment objects, for example tumors, may be recreated for each beam application, each of which may occur from a certain solid angle. This may be important in order to protect adjacent healthy tissue, e.g. positions next to a tumor, to the greatest extent possible. In the case of critical tissue such as nerves, this may be particularly necessary in order to preserve their functional capability.

As indicated above, the rays are generated for treating a predefined body part of a patient. Herein, the predefined body part may be at least one organ or a part of an organ or at least a part of a tumor or a complete tumor and/or cancer cells. Preferably, the predefined body part may be at least a part of the skin and/or at least a part of the head and/or at least a part of the neck and/or at least a part of the breast and/or at least a part of the lung and/or at least a part of the prostate, e.g. a skin tumor and/or a tumor in the head and/or a tumor in the neck and/or a tumor in the breast and/or a tumor in the lung and/or a tumor in the prostate. The patient may, preferably, be a human being, e.g. an adult person or a child, but may also be an animal and/or a plant and/or a phantom, preferably the patient may be a sick person and/or a person which may be treated.

For a purpose of treating a predefined body part of a patient, the rays, preferably the beams, may be collimated and shaped by the collimator in a particularly preferred fashion that the rays may have exactly the same shape as the predefined body part, preferably, the collimator, preferably the multi-leaf collimator, may collimate and shape the rays in a manner that at least one of intensity modulated radiation therapy (IMRT), adaptive radiation therapy (ART), or dynamic radiation therapy may be possible. Herein it may be particularly advantageous if movements of the predefined body part of the patient may be taken into account during the treatment, wherein the movements of the predefined body part of the patient may, for example, be due to breathing and/or sneezing and/or gulping and/or coughing and/or tremor other movements of the patient and/or the predefined body part and/or displacements of the body part due to effects caused by metabolism, such as a filling of the bladder of the patient which may be capable of changing a position of a tumor in the prostate. In addition, imaging capabilities of modern therapeutic devices may be applied here. By way of example, a hybrid radiation therapy device may be combined with an imaging modality, such as a magnetic resonance imaging (MRI) device. Further, image information with respect to patient positioning and internal organ structures may be applied. In addition, a breathing belt may be used in order to follow organ movement and provide a basis for respective predictions. Further, one or more of a respiratory monitor, a surface guided radiotherapy by tracking patients surface in two and/or three dimensions, a 6D skull tracking system, implanted soft tissue (beacon) transponders or two and/or three dimensional kV or MV imaging, in particular of the bony anatomy in order to locate and track tumors, may be used.

As further indicated above, the control device is designated for controlling the at least one collimator. As generally used, the terms "control" and "controlling" comprise an action of managing, commanding, directing or regulating a behavior of at least one further device or system, either on a defined area or on general terms within the system. In particular, this comprises collecting and/or exchanging information, preferably digital information and/or analog information, e.g. voltages and/or currents, with respect to the further device or system. In this regard, the term "control" may also comprise addressing the further device or system with jobs. Information may contain different system parameters that can be influenced by the further device.

In accordance with the present invention, the control device comprises a particular set-up or architecture as expressed in the corresponding independent claim which is, specifically, adapted for controlling the at least one collimator. In this particular set-up, the control device comprises at least three different kinds of partitions and connections between some of the partitions. The control device comprises a programmable logic controller as a first-level partition, a plurality of controller nodes as a second-level partition, and a plurality of device controllers as a third-level partition, wherein the partitions of adjacent levels are connected by at least one real-time bus interface. As generally used, the term "partition" refers to a unit comprised by the control device that may be separable from all other units comprised by the control device by their respective function. A physical separation of the particular unit from any or all other of the units as comprised by the control device may be preferred, in particular as in the embodiments as described below in more detail, but is not required.

As further generally used, the term "level" refers to an arrangement of the various partitions in which a definite relationship between the partitions is provided for. In general, a higher level with respect to an adjacent lower level, such as a first level with respect to a second level, or a second level with respect to a third level, refers to a subordinate relationship of the lower level with respect to the adjacent higher level. Herein, the term "subordinate relationship" describes a relationship between two partitions on different adjacent levels may, in other terms, also denoted as a "master-slave relationship", wherein the partition on the higher level is considered as a master with respect to a slave on the adjacent lower level. Herein, the master is the partition which controls the slave within a defined area by performing actions of managing, commanding, directing or regulating which affect the behavior of the slave within this defined area. Thus, it is emphasized that this particular relationship does not exclude, that, on different adjacent levels, a partition which may acts as a slave in a first relationship within a first area may act as a second master with respect to a second slave on an adjacently lower level within a second area in a second relationship, wherein, however, the second area may, in general, be or comprise more specific actions of managing, commanding, directing or regulating the behavior of the second slave compared to the first area.

Thus, as indicated above, the programmable logic controller which is placed on the first level acts as the master with respect to each of the controller nodes which is placed on the second level, each of which acts, on one hand, as the slave with respect to the programmable logic controller. On the other hand, each of the controller nodes placed on the second level acts as the master with respect to each of the corresponding device controllers being placed on the third level, each of which acts as the slave with respect to the corresponding controller nodes. In order to achieve a smooth and well-functioning of the control device in this particular set-up which is adapted for controlling the at least one collimator, each of the partitions of the control device which are engaged in a definite relationship are, in addition, connected by a real-time bus interface, by which the jobs and information are exchanged between the corresponding partitions placed on the respective levels.

Thus, the programmable logic controller, which may also be abbreviated by the term "PLC", is adapted in order to perform the role of a master device being placed on a first level with respect to each of the controller nodes which are placed on the second level. The controller nodes are, thus, adapted to perform the role of a slave device with respect to the programmable logic controller. As indicated above, the role of the master device as executed by the programmable logic controller may comprise the control and/or command over each of the controller nodes. The role of the slave device as executed by the controller nodes in this regard may comprise execution of at least one command given by the programmable logic controller as the master device. Further, the programmable logic controller performing the role of the master device is connected, preferably for executing of control and for information exchange, with each of the controller nodes in this regard being adapted to perform the role of the slave device.

For this purpose, the programmable logic controller may, preferably, be or comprise a digital computer, which may be designed for multiple input and output arrangements and/or which may be applicable for extended temperature ranges and/or which may provide immunity to electrical noise and/or to vibration and/or to another impact. The programmable logic controller may comprise at least one logic for a control loop, e.g. at least one PID controller, which denominates a proportional, integral, and derivative controller. Herein, a control loop may be used in the controller nodes by implementing at least one of a position control (PID), a velocity control (PI) and/or a torque control (PI) loop. As a result, actual process values such as position, velocity or torque can be retrieved. Thus, a target position, an offset for a torque, a position, or feedforward values for acceleration and velocity can be transferred for use as input values for the control loop. The programmable logic controller may be a system according to the IEC 61131-3 standard, specifically, at the time of application of this document, which is based on the international IEC 61131 standard. The programmable logic controller preferably may comprise at least one software, which preferably may be configured to run an update cycle, which may run within a strict and/or controllable and/or predefined and/or guaranteed cycle time, which preferably has to be met, wherein the update cycle may be repeated preferably continuously. In particular, the programmable logic controller may, thus, be capable of at lest one of providing an interface to a treatment delivery system, data consumption of relevant treatment data, initiating collimator movement and leaf control, supervision of leaf movement and collision detection and prevention, and real-time interface to tumor detection and supervision systems, including but not limited imaging modalities and real-time treatment planning systems. As a result, the programmable logic controller may produce output results in response to input conditions within a deadline, specifically within the update cycle.

Herein, the programmable logic controller may, preferably, be a real-time system, in particular, a hard real-time system. As used herein, the term "real-time system" refers to a system, in which the duration of an operation, e.g. the update cycle and/or a delay time and/or a response time is predefined, such as to a pre-defined maximum duration. Herein, the real-time system may, preferably, execute the update cycle within strict constraints, in particular strict time constraints. The real-time system may be said to have failed if an update cycle is not completed before a deadline, wherein the deadline may be relative to an event for a system to be defined as real-time, it preferably meets its time constraints and/or deadlines. The real-time system and/or one or more deadlines may be classified as "hard real-time" or "soft real-time". Herein, the soft real-time may comprise systems and/or deadlines, wherein usually the deadlines will not be missed. The attribute hard real-time may classify deadlines and/or systems wherein a strict time deadline is guaranteed. Missing a deadline within the hard real-time system may be classified as a total system failure. The goal of the hard real-time system may be to ensure that all time deadlines may be met.

Further, each of the controller nodes is adapted in order to perform the role of a master device being placed on a second level with respect to at least one of the device controllers which are placed on the third level. The device controllers are, thus, adapted to perform the role of a slave device with respect to the controller nodes. As indicated above, the role of the master device as executed by the controller nodes in this regard may comprise the control and/or command over each of the controller nodes. The role of the slave device as executed by the device controllers may comprise execution of at least one command given by the corresponding controller node as the master device. Further, the controller node performing the role of the master device in this regard is connected, preferably for executing of control and for information exchange, with each of the corresponding device controllers being adapted to perform the role of the slave device. In particular, the controller nodes may be able to establish all pre-defined drive profiles as provided by an applicable standard, preferably an industrial standard for CanOpen, being valid, preferably, at the time of filing this document, such as profiles DS401, DS402 and DS406 specified by CiA, implemented via Can over Ethercat (CoE) or other fieldbus systems as DeviceNet, Profibus, Profinet, Interbus, Modbus, or SERCOS.

Herein, each of the device controllers is designed for controlling at least one of an actuator and a sensor, wherein the actuator is designed for adjusting a corresponding part of the collimator, such as a particular axis of a leaf of the collimator, and wherein the sensor is designed for providing data related to position information and/or velocity information with respect to the corresponding part of the collimator, such as to the particular axis of the leaf of the collimator. The term "adjusting" may comprise a control of at least one of the position and/or the direction and/or the velocity (speed) and/or the torque of a part of the collimator, e.g. a regulation and/or a modulation of any one of these physical quantities. Herein, the at least one actuator and/or the at least one sensor may be connected to one of the device controllers. In particular, the particular part of the collimator may be adjusted by applying energy, specifically electrical energy, in order to convert it into motional energy and/or rotational energy. For this purpose, the device controller may comprise at least one of a voltage converter, a voltage modulator, a current converter, a current modulator, a signal transformer or a logical unit. However, further units may also be conceivable.

The actuator is designed for adjusting the respective part of the collimator, in particular an axis of a particular leaf of the collimator. Herein, the parts, such as the leaves, specifically the axes of the leaves, of the collimator may be individually adjustable by an individual actuator. For this purpose, the collimator, preferably the multi-leaf collimator, may comprise at least one set, preferably two sets of displaceable leaves arranged side by side, e.g. facing each other which can be adjusted by at least one actuator in order to impress a high-energy beam, e.g. the rays, with the shape of an irregularly formed treatment object, e.g. the predefined body part and/or the tumor, e.g. by enabling each of the leaves to assume a position oriented along the shape of the treatment object. As used herein, the term "actuator" refers to an arbitrary device which is designated for mechanically moving and/or positioning an element or group of elements.

Thus, the actuator may be selected from the group consisting of a mechanical drive, a piezoelectric actuator and a motor, specifically a linear motor and/or a brushless or brushed DC or AC motor. However, further kinds of actuators may also be feasible. In general, the actuators may be designed to generate driving power which may be needed for motors for adjusting the respective part of the collimator. As a result, the functionality of the actuators can, thus, be reduced to moving the corresponding part of the collimator.

Further, the sensor is designed for determining a position of the corresponding part of the collimator, specifically, of a respective axis of a particular leaf of the collimator. For this purpose, the sensor can be designated as a digital sensor, such as an encoder, or as an analog sensor, such as a potentiometer. However, further kinds of sensors may also be feasible. Preferably, a double amount of sensors compared to an amount of actuators can, in particular, be used for achieving redundancy and verification purposes. As a result, the functionality of the sensors can, thus, be reduced to pure sensor acquisition.

In a preferred embodiment, each of the device controllers can be implemented either as a dedicated actuator controller which is adapted for a control of at least one of the actuators or as a dedicated sensor controller which is adapted for the control of at least one of the sensors. As an alternative preferred embodiment, at least one of the device controllers may comprise a combined actuation and sensor controller which is adapted for a control of at least one of the actuators and of at least one of the sensors. However, irrespective of the selected embodiments, each of the controller nodes is designated to perform a main control loop and only interfaces to the device controllers for actuator control and/or position determination via the real-time bus interface by means of at least one of the actuators or at least one of the sensors, respectively. As a result to such a modularity of the device controllers, the control device can be arranged in a flexible and scalable fashion with respect to any amount of the actuators and/or the sensors which may, particularly, be advantageous for adjusting the leaves of the collimator in a desired manner.

As further indicated above, the partitions of adjacent levels as comprised by the control device are connected by at least one real-time bus interface. Herein, the term "interface" refers to a unit which is adapted for exchanging information between the two partitions of the control device. Herein, the interfaces may be implemented as individual units or as part of a network. For this purpose, the interfaces may apply a known connection technology, preferably an electrical connection, such as Ethernet or Bluetooth, a high speed interface, in particular a Peripheral interface as SPI, hostbus or an external memory bus, via electromagnetic waves, such as via a radio frequency or a High-frequency connection, or a photonic connection, such as optical fibers or optical beam paths. However, further kinds of connections may also be feasible.

Preferably, each partition of the control device, i.e. the programmable logic controller, the plurality of the controller nodes and the plurality of the device controllers, may comprise at least one built-in communication port being adapted for the real-time bus interface, such as for at least one Ethernet connection, preferably by at least one hard real-time Ethernet connection. The control device further may be able to communicate over a network to at least one other system, e.g. to at least one computer, e.g. a PC and/or another calculator. Herein, the hard real-time Ethernet connection may comprise at least one device for connecting the respective units by fulfilling the hard real-time conditions as defined above. The hard real-time Ethernet connection may be defined to provide a guarantee of connection and/or service to consistently operate deterministically and correctly.

The hard real-time Ethernet connection preferably may be a part of a real-time communication network, preferably a hard real-time communication network. Herein, the real-time communication network may comprise at least one circuit and/or at least one junction and/or at least one node. The hard real-time Ethernet connection may comprise a known bus system, such as an EtherCAT (Ethernet for control automation technology) system and/or a DeviceNet, a Profibus, a Profinet, an Interbus, a Modbus, or a SERCOS system. In a particular embodiment, the control device may comprise at least one hard real-time field bus system and, in addition, at least one redundant hard real-time field bus system, e.g. EtherCAT, e.g. as a backup system and/or an additional safety system. EtherCAT in general is a special case of a field bus, preferably EtherCAT may be hard real-time capable. Field bus systems, preferably for industrial applications, e.g. EtherCAT, are standardized worldwide by the IEC 61158 standard. Field bus systems in general are specified in the IEC 61784-1 standard as Communication Profile Families (CPF). Newer real-time capable Ethernet-based field bus systems may be assorted in the IEC 61784-2 standard. In case of doubt, a standard which is valid at the time of application of this document is applicable. Protocol suites may define further field bus systems. The EtherCAT system may be preferably an open high performance Ethernet-based field bus system. Preferably, EtherCAT and/or the hard real-time Ethernet connection may, in particular, be able to provide short data update times, preferably short update cycles, preferably with low communication jitter, e.g. for synchronization purposes. For synchronization, a distributed clock mechanism may be applied, which preferably may lead to very low jitters, e.g. to jitters of significantly less than 1 µs. Thus, the real-time field bus may be able to compensate delay times of information and/or signals and/or communication of actual positions and/or target positon, e.g. delay times caused by different distances and/or different lengths of cables between different partitions of the control device.

In a particular preferred embodiment of the present invention, the control device may be adapted to place one or more of the plurality of the parts of the collimator in a target position. The term "target position" may, preferably, refers to a position to which the actual position can be adjusted. The actual position may be a feedback position and the actual position may, preferably, be regulated to the target position, preferably in a feedback loop. Herein, the target position may, in particular, be at least one static target position and/or at least one dynamic target position. The target position may be constant during an application of a dose in a radiation therapy session, such as during a radiation therapy and/or during a period of the radiation therapy, e.g. during one day and/or one week and/or one month and/or during one sitting. Preferably, the dynamic target position may change during time, e.g. continuously and/or discontinuously, e.g. between different update cycles and/or different periods and/or which may change according to the movements of the patient and/or the movements of the predefined body part as described above in more detail. The dynamic target position may, preferably, be generated by using at least one algorithm predicting the time-development of the target positions, preferably by determining a trajectory of at least one movement of the body part and/or of the patient, such as by predicting a probable movement, such as a movement due to a regular breathing or heartbeat of the patient. Dynamic target positions may, specifically, be used to improve dynamic treatment modes, e.g. as dynamic intensity modulated radiation therapy (IMRT) and/or adaptive radiation therapy (ART) and/or 4D treatment methods, e.g. as gating and/or tumor tracking, preferably, with high position precision and/or time-controlled precision. Herein, the term "tumor tracking" refers to tracking the tumor by shape movement and deformation of the at least one collimator. By way of example, a dynamic target position may be used in a radiation therapy for destroying a tumor and/or for, preferably simultaneously, not destroying healthy parts of the patient.

The algorithm may comprise one or more additional algorithms. The algorithm may be used, at least partially, e.g. to predicting the movements of the patient and/or the movements of the predefined body part of the patient, e.g. by using at least one actual position and/or at least one calibration position. The algorithm may be able to calculate a performance of the therapeutic method, e.g. variations of ray intensities and/or variations of ray positions, for destroying, e.g. the tumor and/or for protecting healthy parts of the patient. Hereby, predicted trajectories of the movements of the body part, such as a breathing frequency and/or the heartbeat may be taken into account. The patient may have position calibration marks, e.g. marked on the skin, preferably for providing known trajectories of the movements of the predefined body part and/or of the patient. The trajectories of the movement may be recorded e.g. by visualization of the marks, e.g. by taking at least one picture and/or acquiring at least one image, e.g. with at least one camera, and/or by continuously imaging the marks and/or comparing the marks by using at least one laser beam and/or at least one laser system. Preferably at least one adjusted target position may be determined by evaluating the acquired images, e.g. the move of the patient and/or the move of the predefined body part, or via a camera or by electromagnetic acquisition when using implanted markers (beacons). Alternatively or additionally, position identifiers may be implemented into the patient, preferably into and/or on and/or next to the predefined body part, to get the trajectories and/or another control parameter. The trajectories may be relative distances compared to a fixed position, such a part of a treatment room, e.g. an isocenter, a table and/or a ray source, and/or the trajectories may be distances.

As the first master device, the control device may be adapted to provide the at least one target position to the controller node which, as the first slave device, is designed for implementing the target position by providing commands, as the second master device, to the device controllers which may be involved for achieving the target position as the second slave devices. Herein, each of the involved device controllers is designed for adjusting the target position by driving the involved actuator and/or by controlling the position and/or velocity by using the corresponding sensor, in particular, whether or to which extent the target positon has been reached by the respective part of the collimator. Thus, for leaf control, both point to point and continuously given new target positions, the controller nodes may, preferably, be adapted to establish to drive to given fixed shapes or to establish permanently dynamic shapes to follow tumor movements in real-time within a cycle time.

Herein, an update cycle may be defined. During one update cycle, all or at least a part of the sensors may provide data being related to position information and/or velocity information with respect to the respective parts of the collimator to the corresponding device controllers which, subsequently, determine position information and/or velocity information with respect to the part of the collimator. This position information and/or velocity information may, subsequently, be forwarded from the involved device controllers as the second slave devices to the corresponding controller node as the second master device which may determine the actual positons of the corresponding part of the collimator from the received position information and/or velocity information. The control device may be adapted such that the update cycle may have a cycle time of no more than 1 ms, preferably of no more than 100 µs, or even no more than 10 µs. Preferably, the cycle time may be smaller than typical time scales in which the predefined body part and/or the patient may move significantly, e.g. at least a distance of the diameter of the predefined body part, preferably at least a distance of 10% of the diameter of the predefined body part, most preferably at least a distance of 1% of the diameter of the predefined body part. Preferably, the cycle time may define the deadline, which may be guaranteed by the real-time system, preferably by the hard real-time system, most preferably by the programmable logic controller.

In case of a deviation between an actual position of the respective part of the collimator and the desired target position which had been provided to the controller nodes (as the first slave device) by the control device (as the first master device), the respective controller nodes (as the second master device) command the corresponding device controllers (as the second slave devices) to perform a required correction. Subsequently, the respective device controller may use a corresponding actuator in order to adjust the corresponding part of the collimator, specifically, a particular axis of a particular leaf of the collimator. In this fashion, at least one control loop which may be adapted for a consecutive control of the actual positions of the parts of the collimator with respect to the desired target positions can be established.

Further, a system clock may be provided, wherein the system clock may be a clock and/or a device, which may be able to provide a clock pulse and/or a beat, preferably a periodic signal, preferably with high accuracy and periodicity. In particular, the system clock may be triggering and/or synchronizing the update cycle. Herein, the system clock may comprise and/or be connected to at least one electronic trigger and/or at least one crystal oscillator and/or at least one atomic clock. The electronic trigger and/or the crystal oscillator and/or the atomic clock may be implemented in a partition of the control device or may be provided by an external device, e.g. by broadcasting a signal, e.g. by using at least one cable and/or a radio frequency signal. Thus, the clock pulse and/or the beat and/or the system clock may be generated in the control device or may be generated, e.g. by an atomic clock outside the control device. Inside the control device, the clock pulse and/or the beat and/or the system clock may be provided by a crystal oscillator, preferably a crystal oscillator which may be able to create an electrical signal, e.g. the beat, with a very precise frequency, e.g. for providing beats with frequencies from about 1 kHz to 100 MHz, specifically from 1 MHz to 50 MHz.

In a particularly preferred embodiment, the control device may comprise, on one hand, at least the programmable logic controller and the controller nodes and, on the other hand, the device controllers and the actuators and/or sensors in connection hereto, as individual physical items. Alternatively, the control device may comprise, on one hand, at least the programmable logic controller and, on the other hand, the controller nodes, the device controllers and the actuators and/or sensors in connection hereto, as individual physical items. In this particularly preferred embodiment, such an allocation of the mentioned partitions may allow arranging predominantly radiation-sensitive partitions of the control device outside a treatment room which may be subject to radiation. The device controllers and the corresponding actuators and/or sensors and, if applicable, the controller nodes may be selected as less radiation-sensitive electronic elements and can, thus, preferably be placed inside the treatment room for performing their respective tasks where they may be subject to radiation. Consequently, intelligent and sensible ability of controlling the parts of the collimator can, thus, be placed outside a sensitive radiation area. The treatment room, e.g. a therapy chamber, for treating the predefined body part of the patient with the rays, may have shield elements, preferably one or more shield elements, for preventing the rays from leaving the treatment room. The shield element preferably may be a device for protecting a passage of the rays and/or for isolating volume from the rays and/or for blocking and/or reflecting and/or absorbing the rays. The shield elements may be divided into several single shield elements. The shield element may comprise at least one material being able to attenuate and/or reflect and/or absorb and/or block the rays. The shield element may comprise at least one material, which filters the rays and/or parts of the rays, which may be dangerous for any devices and/or for the environment and/or for customers, like nurses and/or doctors and/or other medical staff and/or other patients. The shield element may comprise several layers, e.g. wherein each layer may be non-transparent to another part of the rays, e.g. for another frequency range of the rays.

The control device for controlling the at least one collimator according to the present invention provides a large number of advantages over known devices. The control device of the present invention may be able to guarantee real-time capability, preferably hard real-time capability. Herein, the control device may be programmed via industrial standard interfaces with a common language, e.g. provided via IEC 61131-3 standard. The exchangeability of components, e.g. a particular actuator or sensor, may be easier compared to known control devices. Preferably, an exchangeability of used technology, e.g. obsolete technology, with newer one, i.e. more modern technology, may be very easy, preferably without total redesign of the control device. Further, the control device according to the present invention supports and/or comprises real-time, preferably hard real-time, communication bus systems, preferably a hard real-time field bus system.

A distributed allocation of different partitions of the control device as master devices and/or as slave devices may contribute to an improved functionality of the control device, thus, allowing to build a distributed control loop design with a high cycle rate. Preferably, control loop algorithms can established in a meta control layer itself. In addition, the distributed allocation may allow locating radiation-sensitive partitions of the control device outside the treatment room while locating other partitions of the control device inside the treatment room. Thus, on one hand, the programmable logic controller and, if applicable, the controller nodes may be located outside the radiation area, e.g. outside the treatment room, whereby, an increased fail-safe functionality may be established. On the other hand, the device controllers, the actuators and the sensors and, if applicable, the controller nodes can be located inside the radiation area, e.g. inside the treatment room, thus, being close to the parts of the collimator whose positions require being adjusted and controlled. As a result, a compact solution may be obtained in this fashion in which a minimum amount of intelligence is placed in radiation area in which radiation hardness may be required. This compact solution may further contribute to increase maintainability and serviceability as only a limited amount of the control electronic is located in the radiation area, such as by placing easily exchangeable parts in the radiation area which are cheap for exchange, thus allowing preventive maintenance in order to prevent radiation effects.

The present invention may, further, result in a reduction of a complexity and responsibility of a control of components within the radiation area. Preferably, a functionality of a particular component can be reduced to pure sensor acquisition or to pure power output for an actuator. Due to such an obtained less complexity, a reduced price for the components may be achieved, supplemented by easier exchangeability and serviceability.

Additionally, the present invention, following industrial standards, may open a flexibility towards an open architecture and re-usability for different vendors, by using standard interfaces. A usage of a wide range of industrial offered standard devices may be possible as, e.g. so called terminals, by way of example, allowing an application of on-the fly treatment planning systems. The control device according to the present invention may provide standard interfaces to standard needs of controlling of the actuators and of data acquisition by the sensors. As data, e.g. information and/or commands and/or actual positions and/or target positions, according to the present invention, may, preferably, be distributed in real-time, preferably in hard real-time, collision avoidance and/or collision prevention can be established.

Specifically in contrast to WO 2013/014260 A1, the set-up or architecture of the control device according to the present invention is capable of distributing process relevant functionality in dedicated nodes, e.g. a sensor specified for pure sensor acquisition or a dedicated actuator for motion control. This set-up enables minimizing assembly size, specifically, by placing a node directly to the components to be controlled. Further, it minimizes cable distribution by the set-up of the plurality of the real-time bus interfaces. Further, the real-time capability of nodes and the usage of real-time bus interfaces establishes an overall control of all nodes within a fixed cyclic control rate. Herein, actuator node or multi-axis device drivers can provide drive modes which are given by automotive industry CiA standards and can, thus, provide full compatibility to PLC masters.

SHORT DESCRIPTION OF THE FIGURES

Further optional details and features of the present invention may be derived from the subsequent description of preferred embodiments, preferably in combination with the dependent claims. Therein, the respective features may be realized in an isolated way or in arbitrary combinations. The invention is not restricted to the preferred embodiments. One embodiment is depicted schematically in the figure. Identical reference numbers in the figures refer to identical elements or to elements having identical or similar functions or to elements corresponding to each other with regard to their functionality.

Figure 2:
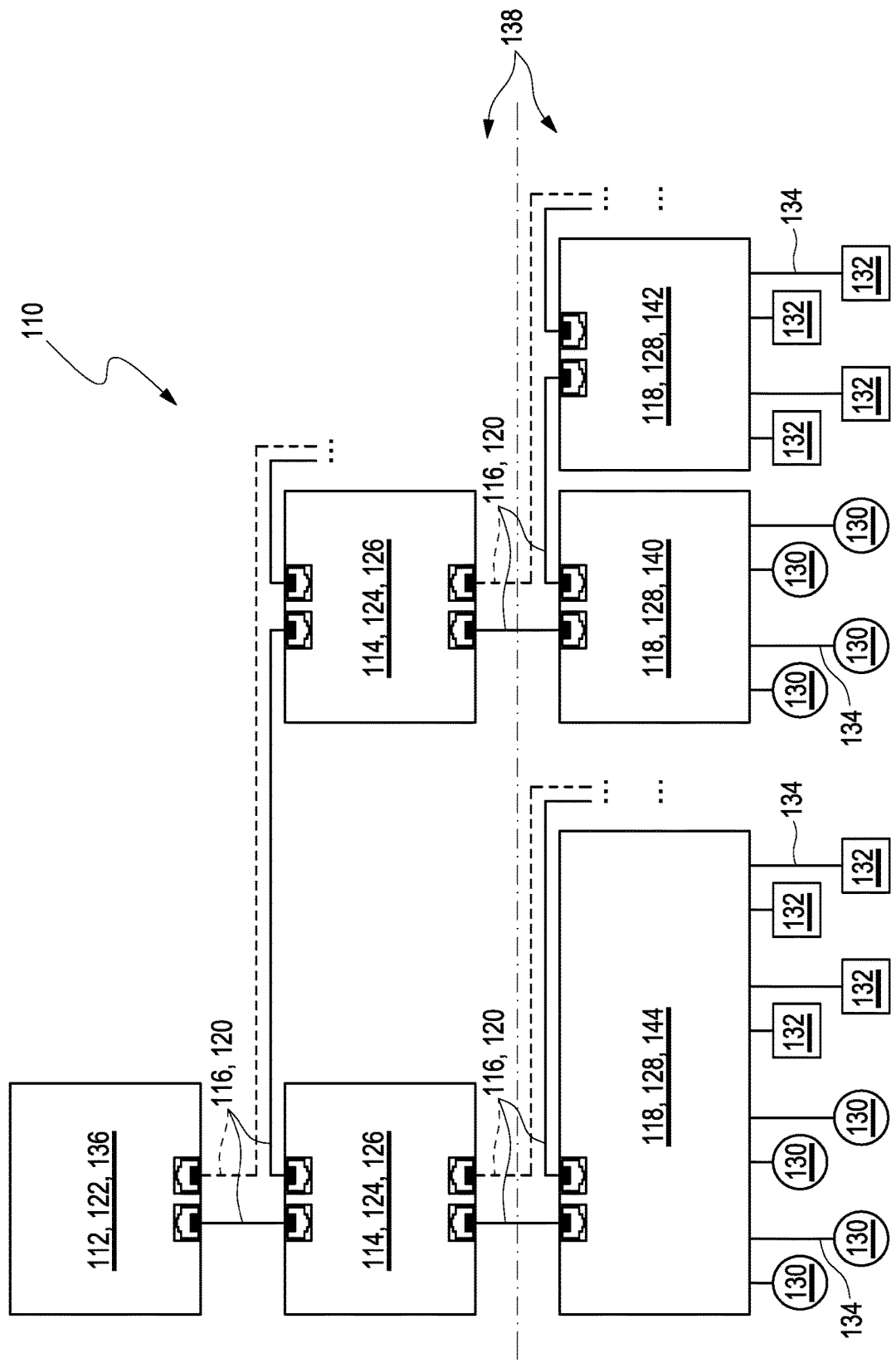
Figure 3:
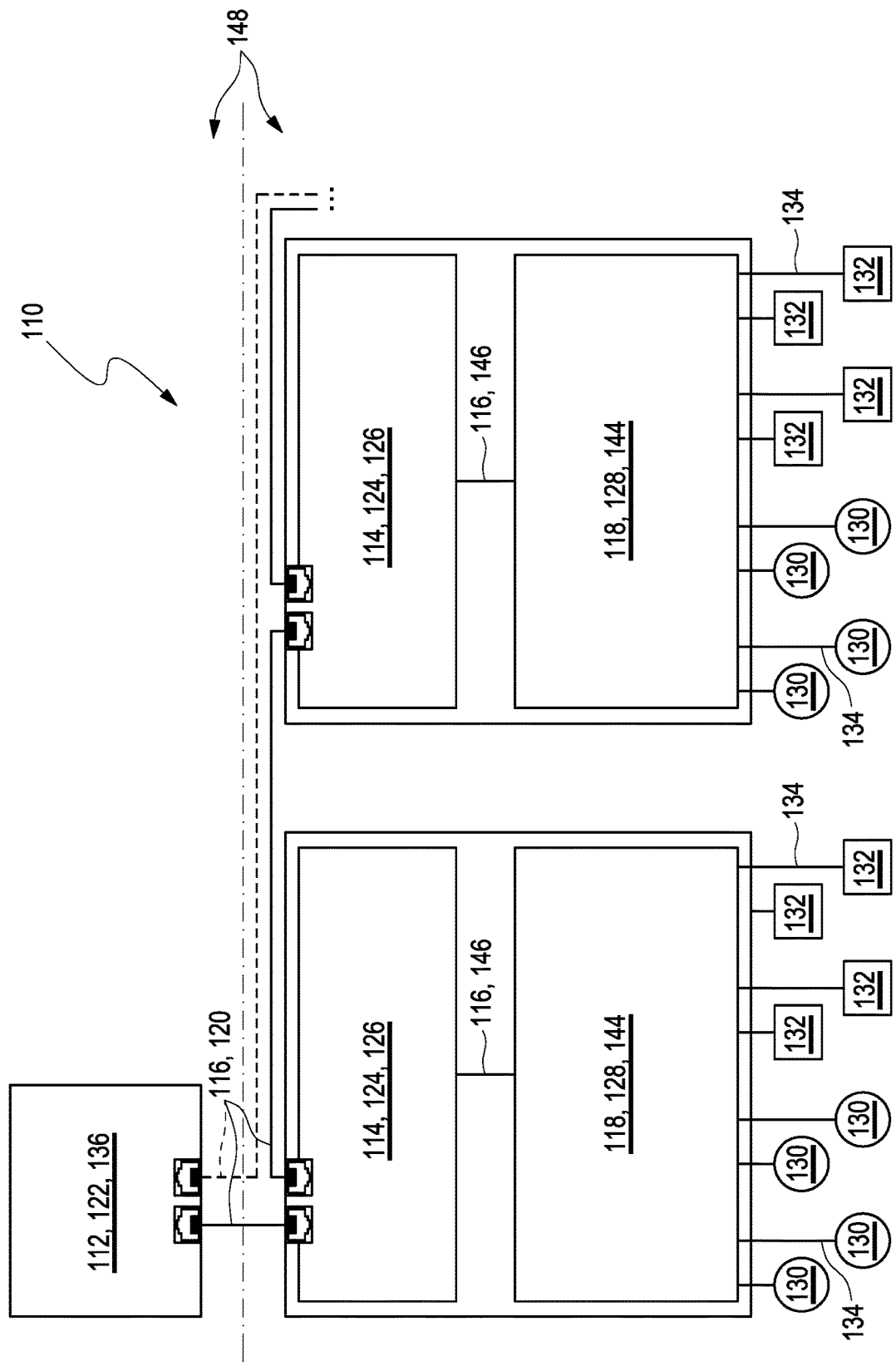

FIG. 1 shows a first preferred embodiment of a control device for controlling at least one collimator; and FIG. 2 shows a further preferred embodiment of a control device for controlling the at least one collimator; and FIG. 3 shows a further preferred embodiment of a control device for controlling the at least one collimator.

DETAILED DESCRIPTION OF THE EMBODIMENTS

FIG. 1 illustrates a preferred embodiment of a control device 110 which is adapted for controlling at least one collimator (not depicted here). As generally used, the collimator has at a plurality of parts being designed for collimating and shaping rays, wherein the rays are generated for treating a predefined body part of a patient. Herein, the rays may be selected from the group consisting of: a narrow beam of electromagnetic radiation; light; ionizing radiation; charged particles; x-rays; γ-rays; ion rays; α-rays; β-rays; neutron-rays; neutral atom rays; electron rays; proton rays; heavy ion rays; and cold atom rays.

The collimator may be or may comprise a multi-leaf collimator, an iris diaphragm collimator, such as described in WO 2006/119796; a pendular collimator, such as described in WO 03/043 698; or another collimator. The collimator, preferably the multi-leaf collimator, may, thus, have at least 60 leaves, at least 80 leaves or at least 100 leaves and more, wherein the leaves may be individually adjustable and/or controllable. The control device 110 may, specifically, be comprised by a therapeutic device which may, preferably, be used in in the field of cancer-treatment. However, other applications are possible.

As schematically depicted in the preferred embodiment of FIG. 1, the control device 110 according to the present invention comprises a programmable logic controller 112 which is connected to two controller nodes 114 by real-time bus interfaces 116. However, more than two controller nodes 114 may be feasible. Further, for each of the controller nodes 114 the control device 110 comprises two device controllers 118 which are connected to the corresponding controller node 114 by further real-time bus interfaces 116. However, more than two device controllers 118 for each of the controller nodes 114 may also be feasible. Preferably, the real-time bus interface 116 may be or comprise at least one hard real-time field bus interface 120, such as a real-time Ethernet connection. However, other kinds of real-time bus interfaces may also be used.

Herein, the programmable logic controller 112 is designated as a first master device 122 with respect to each of the controller nodes 114, each of which is designated as a first slave device 124 with respect to the programmable logic controller 112. The programmable logic controller 112 is designed for superordinate control of the parts of the collimator which are designed for collimating and shaping the rays designated for treating the predefined body part of the patient, thereby using collision supervision in order to prevent a collision of different parts of the collimator.

As indicated above, each of the controller nodes 114 is designated as the first slave device 124 with respect to the programmable logic controller 112. Further, each of the controller nodes 114 is designated as a second master device 126 with respect to at least one corresponding device controller 118, each of which is designated as a second slave device 128 with respect to the corresponding controller node 114. Each of the controller nodes 114 is designed for controlling a plurality of corresponding parts of the collimator.

Thus, each of the device controllers 118 is designated as a second slave device 128 with respect to the corresponding controller node 114 which acts as the corresponding second master device 126. Herein, each of the device controllers 118 is designed for controlling at least one of an actuator 130 and a sensor 132, wherein each of the actuators 130 and sensors 132 may be connected to the corresponding device controller 118 by a connection 134 which may be a direct or a wireless connection, wherein the wireless connection may use a particular kind of electromagnetic radiation, such as visible light, infrared radiation, HF frequencies, or radio waves, for data exchange. In general, the device controllers 118 may be implemented as single control units or, as an alternative, be deployed on a common control unit, hereby, providing a multi-device controller 118.

Herein, each of the actuators 130 is designed for adjusting the corresponding part of the collimator, in particular the respective axis of a particular leaf of the collimator. For this purpose, each of the actuator 130 may comprise at least one of a linear or a rotational driving unit, preferably a servo drive, which may be adapted for this purpose. Herein, the driving units as comprised by each of the actuators 130 are designed to generate driving power which may be needed for motors which actually adjust the respective part of the collimator. In particular, each of the actuators 130 may be or comprise a brushless or brushed DC or AC motor or a stepper motor, a linear motor, or a piezo drive. As a result, it can, thus, provide a cascaded position and velocity control having a 3 kHz and a 32 kHz current control loop. However, further kinds of actuators 130 may also be feasible. As a result, the functionality of the actuators 130 can, thus, be reduced to moving a corresponding part of the collimator.

Further, each of the sensors 132 is designed for determining a position of the respective part of the collimator, in particular for a position detection of one or more axes of the leaves of the collimator. For this purpose, the sensor 132 can be designated as a digital sensor having incremental encoders exhibiting a resolution up to 32 bit at approx. 10 MHz or as an analogue sensor, such as a potentiometer, having a resolution of approx. 12 bit at approx. 10 kHz. However, further kinds of sensors 132 may also be feasible. In the preferred embodiment as depicted in FIG. 1, a double amount of sensors 132 compared to an amount of actuators 130 is preferred, in particular for achieving redundancy and verification purposes. As a result, the functionality of the sensors 132 can, thus, be reduced to pure sensor acquisition.

As schematically illustrated in FIG. 1, each of the device controllers 118 in the preferred exemplary embodiment as shown therein may be implemented either as a dedicated actuator controller 140 or as a dedicated sensor controller 142. In contrast hereto, FIG. 2 schematically illustrates a further preferred embodiment of the control device 110 which at least one of the device controllers 118 comprises a combined actuation and sensor controller 144. However, in both embodiments, each of the controller nodes 114 is designated to perform a main control loop and only interfaces to device controllers 118 for actuator control and/or position determination via the real-time bus interface 116 by means of at least one of the actuators 130 or at least one of the sensors 132, respectively.

Preferably, the programmable logic controller 112 may be a real-time system, preferably a hard real-time system 136. Herein, the programmable logic controller 112 may be a computer system which may be typically used for automation of electromechanical processes, such as e.g. control of machinery and/or factory assembly lines. The programmable logic controller 112 may be of a type of programmable logic controllers which can also be used in various industrial, automation and machine applications. Unlike general-purpose computers, programmable logic controllers can be designed for providing multiple input and output arrangements and/or extended temperature ranges and/or immunity to electrical noise and/or resistance to vibration and/or resistance to impact. Programs to control machine operation of the programmable logic controller 112 or of any or all further parts of the control device 110, in particular the controller nodes 114, the real-time bus interfaces 116, and the device controllers 118, can, typically, be stored in battery-baked and/or non-volatile memory.

The real-time system, preferably a hard real-time system 136, of the programmable logic controller 112 may, specifically, allow generating output results in response to input conditions within a time span bordered by a borderline, preferably a deadline, otherwise, unintended operation may be a result. The programmable logic controller 112 may be programmed via standard-based programming languages. Preferably, the programmable logic controller 112 may be a system according to the IEC 61131-3 standard. The programmable logic controller 112 may include logic for at least one single-variable feedback analog control loop and/ or at least one other control loop. Preferably, the programmable logic controller 112 may comprise at least one NC (numerical controller), e.g. at least one PID ("proportional, integral, derivative") controller. As a result, the control device 110 of the present invention may improve and/or may establish dynamic control and/or synchronization of all used parts in the collimator.

The programmable logic controller 112 may be designed to control, in addition to the controller nodes 114, at least one of a linear particle accelerator handling system, e.g. a gantry system; a patient support system, e.g. a patient couch and/or a bed; an x-ray beam generation system, e.g. a ray source; at least one static patient set-up aid; and a control console.

In the preferred embodiment as shown in FIG. 1, the control device 110 may comprise, on one hand, at least the programmable logic controller 112 and the controller nodes 114 and, on the other hand, the device controllers 118 and the actuators 130 and/or sensors 132 in connection hereto, as individual physical items. In a particularly preferred embodiment of the present invention, such a distributed allocation 138 of the mentioned partitions of the control device 110 may allow arranging at least the predominantly radiation-sensitive programmable logic controller 112 and controller nodes 114 outside a treatment room which may be subject to radiation. For this purpose, the treatment room may have at least one shield element for preventing the rays from leaving the treatment room, preferably for preventing the health of people being outside the treatment room and/or for preventing disturbing electronic elements outside the treatment room. The device controllers 118 and the corresponding actuators 130 and/or sensors 132 may be selected as less radiation-sensitive electronic elements and can, thus, preferably be placed inside the treatment room for performing their respective tasks where they may be subject to radiation. Consequently, intelligent and sensible ability of controlling the parts of the collimator can, thus, be placed outside a sensitive radiation area.

The control device 110 may be adapted to place one or more of the plurality of the parts of the collimator as a target position. Herein, the target position may, in particular, be at least one static target position and/or at least one dynamic target position. The dynamic target position may, preferably, be generated by using at least one algorithm predicting the time-development of the target positions, preferably by using at least one predicted trajectory of at least one movement of the body part and/or of the patient. Dynamic target positions may, specifically, be used to improve dynamic treatment modes, e.g. as dynamic intensity modulated radiation therapy (IMRT) and/or adaptive radiation therapy (ART), and/or 4D treatment methods, e.g. as gating and/or tracking, preferably with high position precision and/or time-controlled precision.

Further, the control device 110 may, as the first master device 122, be adapted to provide the at least one target position to the controller node 114 which is, as the first slave device 124, designed for implementing the target position by providing commands, as the second master device 126, to the device controllers 118 which may be involved for achieving the target position as the second slave devices 128. Herein, each of the involved device controllers 118 is designed for adjusting the target position by driving the involved actuator 130 and/or by controlling the position by using the corresponding sensor 132, in particular, whether or to which extent the target positon has been reached by the respective parts of the collimator.

Herein, an update cycle may be defined. During one update cycle, all or at least a part of the sensors 132 may provide data being related to position information and/or velocity information with respect to the axes of the part of the collimator to the corresponding device controllers 118 which, subsequently, determine position information and/or velocity information with respect to the corresponding parts of the collimator. This position information and/or velocity information is, subsequently, forwarded from the involved device controllers 118 as the second slave devices 128 to the corresponding controller node 114 as the second master device 126, which determines the actual positons of the corresponding part of the collimator from the received position information. In addition, all such process values, whether related to actual data or to target values, can be transferred synchronously to the programmable logic controller 112 during the update cycle. As a result, all controller nodes 114 have access to the same process data after a particular update cycle.

In case of a deviation between an actual positon of a part of the collimator and the desired target position which had been forwarded to the controller nodes 114 as the first slave device 124 by the control device 110 as the first master device 122, the respective controller nodes 114 in their function of the second master device 126 command the corresponding device controllers 118 in their function of the second slave devices 128 in order to perform a required correction. For this purpose, a control loop may be used in the controller nodes 114 by implementing at least one of a position control (PID), a velocity control (PI) and/or a torque control (PI) loop. As a result, actual process values such as position, velocity or torque can be retrieved in this manner. Thus, a target position, an offset for a torque, a position, or feedforward values for acceleration or velocity can be transferred to be used as one or more input values for the control loop. Subsequently, the respective device controller 118 may drive a linear driving unit and/or a rotational driving unit as comprised by the corresponding actuator 130 in order to actually adjust the respective part of the collimator, in particular a corresponding axis of a particular leaf of the collimator. In this fashion, a control loop for a consecutive control of the actual positions of the respective parts of the collimator with regard to the target positions may be established.

Herein, the update cycle may have a cycle time of no more than 1 ms, preferably of no more than 100 µs, or no more than 1 ms. For this purpose, a system clock may be provided, wherein the system clock may comprise and/or be connected to at least one electronic trigger and/or at least one crystal oscillator and/or at least one atomic clock. The electronic trigger and/or the crystal oscillator and/or the atomic clock may be implemented in a partition of the control device 110 or may be provided by an external device, e.g. by broadcasting a signal, e.g. by using at least one cable and/or a radio frequency signal.

FIG. 3 shows a further preferred embodiment of the control device 110 for controlling the at least one collimator. In contrast to the embodiments as schematically depicted in FIGS. 1 and 2, each of the two controller nodes 114 and the corresponding device controller 118 as illustrated therein are implemented as individual physical items with respect to the programmable logic controller 112, wherein the real-time bus interfaces 116 between each of the two controller nodes 114 and the corresponding device controller 118 are provided in form of a high speed bus interface 146 which may, preferably, comprise a peripheral interface, such as an SPI, a hostbus, or an external memory bus. However, other kinds of high speed bus interfaces 146 may also be feasible. As a result of this set-up of the control device 110, a different distributed allocation 148 of the mentioned partitions of the control device 110 as shown in FIG. 3 can, thus, be achieved.

LIST OF REFERENCE NUMBERS 110 control device
112 programmable logic controller
114 controller node
116 real-time bus interfaces
118 device controller
120 hard real-time field bus interface
122 first master device
124 first slave device
126 second master device
128 second slave device
130 actuator
132 sensor
134 connection
136 hard real-time system
138 distributed allocation
140 actuator controller
142 sensor controller
144 combined actuator and sensor controller
146 high speed bus interface
148 distributed allocation

The invention claimed is:

1. A control device for controlling at least one collimator, wherein the collimator has a plurality of parts being designed for collimating and shaping rays, wherein the rays are generated for treating a predefined body part of a patient, wherein the control device comprises
a programmable logic controller,
a plurality of controller nodes,
a plurality of device controllers, and
a plurality of real-time bus interfaces,
wherein the programmable logic controller is designated as a first master device with respect to each of the controller nodes, wherein the programmable logic controller is designed for superordinate control of the plurality of parts of the collimator, wherein each of the controller nodes is designated as a first slave device with respect to the programmable logic controller, wherein the controller node is designated as a second master device with respect to at least one corresponding device controller, wherein the controller node is designed for controlling at least one corresponding part of the collimator, wherein the controller node is connected to the programmable logic controller by one of the real-time bus interfaces, wherein each of the device controllers is designated as a second slave device with respect to a corresponding controller node, wherein each of the device controllers is designed for controlling at least one of an actuator and a sensor, wherein the actuator is designed for adjusting a corresponding part of the collimator, and wherein the sensor is designed for providing data related to at least one of position information or velocity information with respect to the corresponding part of the collimator, wherein the device controller is connected to the corresponding controller node by one of the real-time bus interfaces.

2. The control device of claim 1, wherein the device controller is designed as an actuator controller for individually controlling at least one of the actuators or as a sensor controller for individually controlling at least one of the sensors.

3. The control device of claim 1, wherein the device controller is a combined actuator and sensor controller which is designed for controlling at least one of the actuators and at least one of the sensors.

4. The control device of claim 1, wherein the programmable logic controller is designed for placing at least one position of at least one of the parts of the collimator in a target position, wherein the controller node is designed for implementing the target position by providing commands to at least one of the device controllers, wherein the device controller is adapted for commanding the target position to at least one of the actuators and by controlling the position by using at least one of the sensors.

5. The control device of claim 4, wherein the programmable logic controller is adapted to provide a static target position or a dynamic target position.

6. The control device of claim 5, wherein the programmable logic controller is adapted to generate the dynamic target position by using at least one algorithm predicting the time-development of the target position.

7. The control device of claim 6, wherein the programmable logic controller is adapted to determine the probable time-development of the target position by taking into account at least one movement of the predefined body part of the patient.

8. The control device of claim 1, wherein an update cycle is defined, wherein, during a single update cycle, all actual positions are provided to the programmable logic controller and wherein target positions are provided to at least one of the controller nodes by the programmable logic controller.

9. The control device of claim 8, wherein, during the single update cycle, the at least one of the controller nodes which received at least one of the target position by the programmable logic controller command the corresponding device controllers to drive at least one of a linear driving unit or a rotational driving unit comprised by the corresponding actuator to adjust the respective part of the collimator.

10. The control device of claim 1, further providing a system clock, wherein the programmable logic controller is adapted to communicate with the controller nodes and wherein the controller nodes are adapted to communicate with the device controllers in predefined time intervals defined by the system clock.

11. The control device of claim 1, wherein the real-time bus interface comprises a hard real-time field bus interface.

12. The control device of claim 1, wherein the programmable logic controller is a system according to the IEC 61131-3 standard.

13. He control device of claim 1, wherein the collimator is a multi-leaf collimator, wherein the parts of the collimator are collimating leaves being designed for blocking the rays.

14. The control device of claim 13, wherein the position of each of the collimating leaves is individually adjustable by at least one of the actuators and individually controllable by at least one of the sensors.

15. The control device of claim 1, wherein the programmable logic controller and the plurality of the controller nodes are placed outside a treatment room and wherein the plurality of the device controllers, the plurality of the actuators and the plurality of the sensors are placed inside a treatment room, wherein the treatment room is designed for treating the predefined body part of the patient with the rays, wherein the treatment room has shield elements for preventing the rays from leaving the treatment room.

16. The control device of claim 1, wherein the programmable logic controller is placed outside the treatment room, and wherein the plurality of the controller nodes, the plurality of the device controllers, the plurality of the actuators and the plurality of the sensors are placed inside a treatment room, wherein the treatment room is designed for treating the predefined body part of the patient with the rays, wherein the treatment room has shield elements for preventing the rays from leaving the treatment room.

* * * * *